(12) United States Patent
Min et al.

(10) Patent No.: US 9,089,479 B2
(45) Date of Patent: Jul. 28, 2015

(54) MEDIUM, SOLUTIONS AND METHODS FOR THE WASHING, CULTURING AND STORAGE OF WHITE BLOOD CELLS

(75) Inventors: Kyungyoon Min, Kildeer, IL (US); Katherine Radwanski, Des Plaines, IL (US)

(73) Assignee: Fenwal, Inc., Lake Zurich, IL (US)

( * ) Notice: Subject to any disclaimer, the term of this patent is extended or adjusted under 35 U.S.C. 154(b) by 67 days.

(21) Appl. No.: 13/459,511

(22) Filed: Apr. 30, 2012

(65) Prior Publication Data

US 2012/0282234 A1 Nov. 8, 2012

Related U.S. Application Data

(60) Provisional application No. 61/482,119, filed on May 3, 2011.

(51) Int. Cl.
| A61K 9/00 | (2006.01) |
| A61K 35/14 | (2015.01) |
| A01N 1/02 | (2006.01) |

(52) U.S. Cl.
CPC ............ *A61K 9/0026* (2013.01); *A01N 1/0226* (2013.01); *A61K 35/14* (2013.01)

(58) Field of Classification Search
None
See application file for complete search history.

(56) References Cited

U.S. PATENT DOCUMENTS

| 4,923,797 | A | 5/1990 | Babior |
| 5,360,542 | A | 11/1994 | Williamson, IV et al. |
| 5,569,579 | A | 10/1996 | Murphy |
| 5,908,742 | A | 6/1999 | Lin et al. |
| 6,027,657 | A | 2/2000 | Min et al. |
| 6,866,992 | B2 | 3/2005 | Lin et al. |
| 7,488,574 | B2 * | 2/2009 | Oguni ............................ 435/4 |
| 2009/0191537 | A1 | 7/2009 | Mayaudon |
| 2011/0117647 | A1 | 5/2011 | Mayaudon |
| 2011/0238030 | A1 * | 9/2011 | Sano ............................ 604/410 |

FOREIGN PATENT DOCUMENTS

EP 2077074 A2 7/2009

OTHER PUBLICATIONS

Lecoeur et al., Journal of Immunological Methods 209 (1997), pp. 111-123.*
EP Communication with European Search Report for EP Application No. 12 16663 dated Aug. 9, 2012.
Tobian, A., et al.,"Prevention of allergic transfusion reactions to platelets and red blood cells through plasma reduction", Transfusion, vol. 49, pp. 199-201, 2009.
Bertolini, F., et al., "Role of acetate during platelet storage in a synthetic medium", Transfusion, vol. 32, pp. 152-156, 1992.
VandenBroeke, T., et al., "Platelet storage solution effects on the accuracy of laboratory tests for platelet function: a multi-laboratory study", Vox Sanguinis, vol. 86, pp. 183-188, 2004.
Hirayama, J., et al., "Storage of platelets in a noval additive solution (M-sol), which is prepared by mixing solutions approved for clinical use that are not especially for platelet storage", Transfusion, vol. 47, pp. 960-965, 2007.
Radwanski, K., et al., "Apheresis Platelets Store successfully with 10% Plasma in Reformulated PAS with Bicarbonate" Abstracts from the American Society for Apheresis $31^{st}$ Annual Mts. May 26-29, 2010, Journal of Clinical Apheresis. vol. 25, pp. 1-2, 2010.
Springer, W. et al., "Evaluation of a New Reagent for Preserving Fresh Blood Samples and Its Potential Usefulness for Internal Quality Controls of Multichannel Hematology Analyzers",American Journal of Clinical Pathology, vol. 111, No. 3, pp. 387-396, Mar. 1, 1999.
Radwanski, K., et al., "Apheresis Platelet Concentrates Can Be Collected in 5% Plasma with 95% PAS-5 and Stored for at Least 7 Days", Transfusion, vol. 50 Supl. 2, S95-40A Abstract Presentations from AABB Annual Meeting Baltimore, MD, Oct. 9-12, 2010.
Radwanski, K., et al., "Storage of Aphersis Platelets with Low Residual Plasma in Reformulation PAS with Bicarbonate", Vox Sanguinis, vol. 99, Supl. 1, P-0347, pp. 220-221 Abstracts of the XXXIst International Congress International Society of Blood. Transfusion in joint cooperation with the $43^{rd}$ Congress of the DGTI, Berlin DE, Jun. 26-Jul. 1, 2010.

* cited by examiner

*Primary Examiner* — Allison Fox
*Assistant Examiner* — Yvonne Pyla
(74) *Attorney, Agent, or Firm* — Cook Alex Ltd.

(57) ABSTRACT

White blood cell products and storage media for white blood cells are disclosed. The storage medium includes sodium chloride, sodium acetate, sodium citrate, sodium phosphate, magnesium chloride, potassium chloride, sodium bicarbonate, and glucose. White blood cells stored in such medium remain viable for at least up to 72 hours.

12 Claims, 8 Drawing Sheets

MEDIUM, SOLUTIONS AND METHODS FOR THE WASHING, CULTURING AND STORAGE OF WHITE BLOOD CELLS

CROSS-REFERENCE TO RELATED APPLICATIONS

This application claims the benefit of U.S. Provisional Application Ser. No. 61/482,119, filed May 3, 2011, the contents of which are incorporated herein by reference.

FIELD OF THE DISCLOSURE

The present disclosure relates to storage media and solutions for blood components such as white blood cells. More specifically, the present disclosure relates to white blood cell products that include white blood cells and a synthetic solution. The solution may be used in the culturing, storing, washing and processing of white blood cells.

BACKGROUND

Whole blood is made up of various cellular components such as red blood cells, white blood cells and platelets suspended in its liquid component, plasma. Whole blood can be separated into its constituent components (cellular or liquid), and the desired separated component can be administered to a patient in need of that particular component. For example, platelets can be removed from the whole blood of a healthy donor, collected, and later administered to a cancer patient whose ability to "make" platelets has been compromised by chemotherapy or radiation treatment.

White blood cells, sometimes referred to as leukocytes, are nucleated cells that play an important role in the human immune system. White blood cells protect the body's cells and tissue from foreign agents, infections and the like.

Leukocytes can be divided into three (3) groups, namely, granulocytes, monocytes and lymphocytes. (Granulocytes may further be subdivided into neutrophils, eosinophils and basophils.) Monocytes and lymphocytes are sometimes also referred to as mononuclear cells (MNC) because of their single lobed cell nucleus.

While white blood cells have routinely been separated from whole blood, their use as a component for later administration to a patient has not been as widely practiced when compared to other blood components such as red blood cells and platelets. However, recent advances in the medical community's understanding of the relationship between the immune system and the treatment of disease, such as certain cancers, CTCL and other disorders has focused more attention on the collection and use of white blood cells. White blood cells and, more specifically, mononuclear cells are increasingly being considered for use in therapeutic treatments of patients suffering from disease. White blood cells that have been separated as part of a whole blood separation process are, with greater frequency, being collected and later cultured or otherwise activated into cellular agents for use in the treatment of certain diseases.

Inasmuch as white blood cells typically only have a limited shelf life, (when kept at room temperature) they must be administered or otherwise used or cryopreserved soon after their collection. When cells are kept outside the body, they begin undergoing apoptosis, a form of cell death. However, use within 24 hours often proves to be logistically impractical, particularly where the white blood cells may have to be delivered to a different location or may have to be subjected to a culturing, treating or other processing step. Thus, white blood cells are often stored in a storage medium that helps maintain the viability of the white blood cells. Currently, the storage medium RPMI1640 is widely used in the storage (and culturing) of white blood cells. RPMI1640 is a complex storage medium that has been developed for culturing leukocytes and often requires some supplementation with human serum. In addition to its inorganic components, RPMI1640 further includes approximately 20 amino acids and 12 vitamins. As such, white blood cells stored in RPMI1640 cannot be readily transfused, but must typically be washed to remove the storage medium from the white blood cell product.

Storage media for the preservation of blood cells, blood fragments or other blood components are known. For example, synthetic media for the storage of platelets are disclosed in U.S. Pat. Nos. 5,569,579 (Murphy) and 5,908,742 (Lin et al.), which are incorporated herein by reference. InterSol®, a commercially available platelet storage medium is generally described in U.S. Pat. No. 5,908,742, the contents of which are incorporated by reference herein in its entirety. InterSol® contains sodium citrate, sodium acetate, sodium phosphate and adjusted to iso-osmolarity with sodium chloride.

Further examples of media useful in the storage of blood components, such as platelets, are described in U.S. Patent Application Publication No. US2009/0191537A1, filed Dec. 18, 2008, the contents of which are incorporated herein by reference and International Patent Application Serial No. PCT/US2012/32551, filed Apr. 6, 2012, the contents of which are likewise incorporated herein by reference. Storage media for red blood cells are described in U.S. Patent Application Publication No. US2011/0117647, the contents of which are also incorporated herein by reference. The solutions described above are typically readily transfusible to the patient.

While the solutions described above have worked satisfactorily for platelets and other blood components, synthetic solutions suitable for storing white blood cells and that maintain white blood cell viability and are readily transfusible to a patient are not widely available.

Thus, it would be desirable to provide a white blood cell product wherein the viability of the white blood cells is maintained in excess of 24 hours, so that the white blood cells can be used for subsequent administration to a patient.

In addition, it would be desirable to provide a medium that can be used for the storage of white blood cells and that can be readily transfused to a patient. In other words, it would be desirable to provide a readily transfusible white blood cell product (i.e., cells and medium).

Furthermore, it would be desirable to provide a storage solution or solution or medium that can be used to wash white blood cells, to remove any undesired agents or components of a storage medium such as those used in the culturing of white blood cells.

In addition, it would be desirable to provide a storage medium or solution that can itself be used as a culture medium or as part of a culture medium in combination with certain culturing components, such as human serum.

White blood cell products and the storage solutions and media used in such white blood cell products are described in greater detail below.

SUMMARY

In one aspect, the present disclosure is directed to a white blood cell product comprising white blood cells and a medium including a synthetic aqueous solution that includes approximately 45-125 mM of sodium chloride, approximately 5-15 mM sodium citrate, approximately 20-40 mM sodium acetate, approximately 0.05 to about 12 mM of phosphate, approximately 0.05 to about 3 mM magnesium ion, approximately 0.05 to about 10 mM potassium chloride, approximately 5 to about 40 mM of sodium bicarbonate, and approximately 0.5 to about 30 mM of glucose.

In another aspect, the present disclosure is also directed to a method of processing white blood cells, including introducing white blood cells from a source into a blood separation device, separating supernatant from the white blood cells in the device to obtain concentrated white blood cells. The method further includes combining the concentrated white blood cells and resuspending or reconstituting the concentrated white blood cells in a volume of additive solution that includes approximately 45-125 mM of sodium chloride, approximately 5-15 mM sodium citrate, approximately 20-40 mM sodium acetate, approximately 0.05 to about 12 mM of phosphate, approximately 0.05 to about 3 mM magnesium ion, approximately 0.05 to about 10 mM potassium chloride, approximately 5 to about 40 mM of sodium bicarbonate, and approximately 0.5 to about 30 mM of glucose.

DESCRIPTION OF THE ILLUSTRATED EMBODIMENTS

Figure 1:
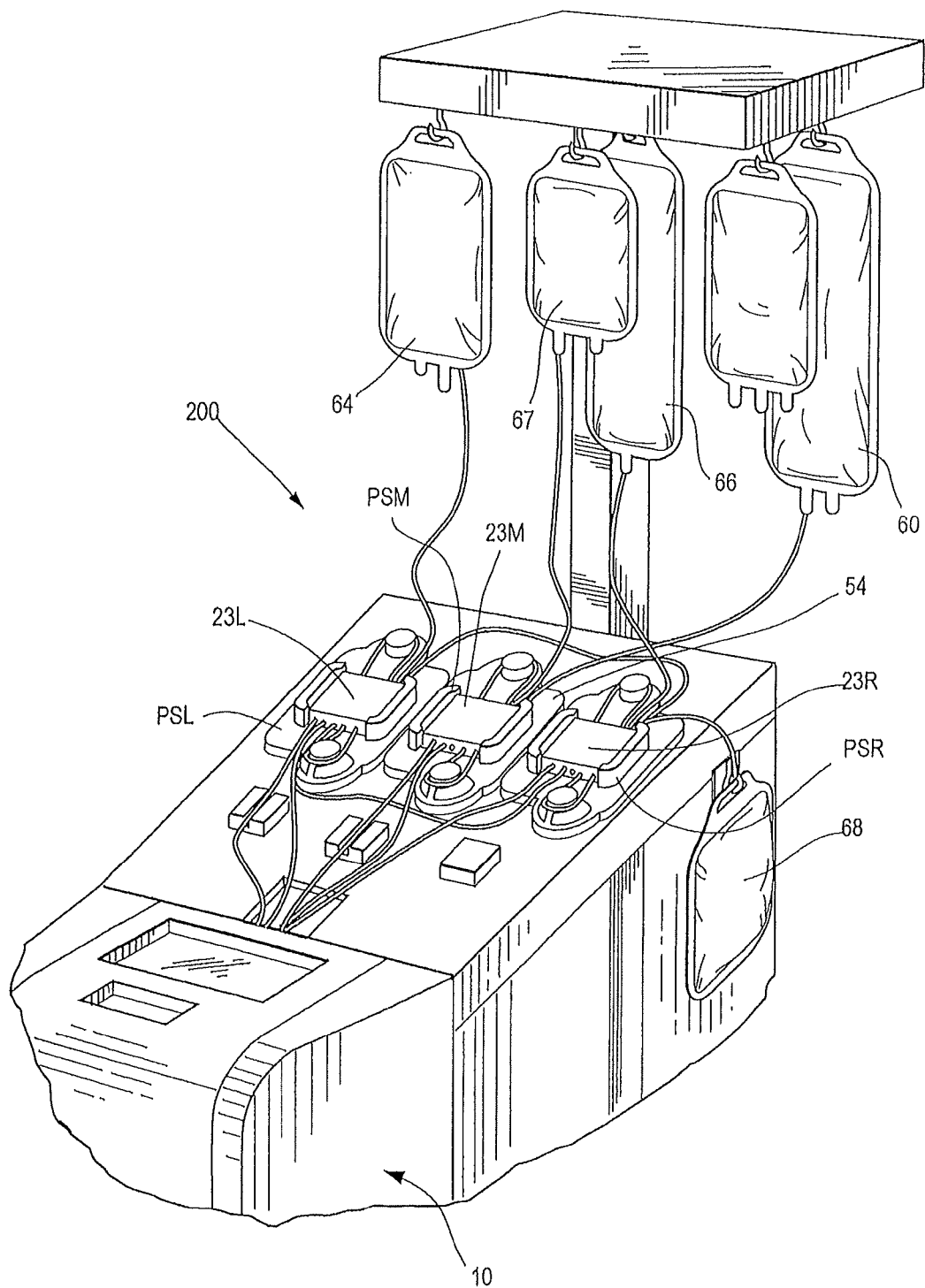
FIG. 1 is a perspective view of an exemplary apheresis device useful in the collection of white blood cells such as mononuclear cells.

The embodiments disclosed herein are for the purpose of providing a general description of the blood products, storage media, methods and systems for storing and processing blood components that are the subject of this disclosure. These embodiments are only exemplary, and may be provided in various forms. Therefore, specific details disclosed herein are not to be interpreted as limiting the subject matter of the invention which is set forth in the accompanying claims.

The white blood cell product described herein includes at least white blood cells and a synthetic aqueous solution and, typically, some amount of plasma. The synthetic solution, plasma and any other additives make up the storage medium for the white blood cells. Thus, white blood cell products described herein include the storage media and the white blood cells stored therein.

Typically, a white blood cell product may have a volume of between about 5-500 ml. The concentration of white blood cells may be between approximately $0.1\text{-}500 \times 10^6$/ml. Where the white blood cell product includes a storage medium (without additives such as human serum used in culturing), the concentration of white blood cells may be anywhere within the above stated range, such as, but not limited to $10\text{-}500 \times 10^6$/ml. Where the white blood cell product includes a storage medium for culturing, the concentration may be closer to the lower end of the $0.1\text{-}500 \times 10^6$/ml range, such as, but not limited to $1\text{-}2 \times 10^6$/ml. As noted above, the white blood cell product may include some residual plasma as part of the storage medium, although typically the amount of plasma (for storage purposes) is 1% or less of the total white blood cell product.

In one embodiment, a white blood cell product is provided that includes an aqueous storage solution that includes one or more nutrients and buffer(s) in a salt solution. The buffer(s), one of which may be a phosphate buffer may include a lower concentration (as compared to InterSol® or other storage solution or media for other components) of phosphate in the platelet storage medium. Additional buffering may be provided by a selected concentration of bicarbonate ion. Bicarbonate may be provided as sodium bicarbonate.

Thus, an embodiment of the synthetic aqueous storage solution described herein and useful for the storage of white blood cells for over 24 hours and up to at least about 72 hours may include about or approximately: 45-120 mM sodium chloride; 5-15 mM sodium citrate; 20-40 mM sodium acetate; 0.5-12 mM phosphate buffer; 0.05-3 mM magnesium ion (provided as, for example, magnesium chloride); and 0.5-30 mM glucose, with the initial pH of the complete storage media ranging from 6.8-7.3. The pH of the solution is approximately 6.5-7.5. Optionally, 0.05-3 mM calcium chloride and/or 0.05-10 mM potassium chloride may also be present in the synthetic platelet storage solution. The aqueous storage solution may (optionally) further include about or approximately 5-40 mM of sodium bicarbonate.

In a more specific embodiment, the sodium chloride of the synthetic aqueous storage solution described above may be present from about 50 mM to about 110 mM. More particularly, the sodium chloride may be present from about 58 mM to about 90 mM or from about 65 mM to about 80 mM. In one embodiment, the concentration of sodium chloride in the final (combined) aqueous solution may be about or approximately 69 mM.

Also, more preferably, the sodium citrate may be present from about 7 mM to about 13 mM, and more typically from about 9 mM to about 12 mM. In one embodiment, the concentration of sodium citrate in the final (combined) aqueous solution may be about or approximately 10 mM.

As set forth above, the storage solution may also include an amount of sodium acetate. In one embodiment the sodium acetate may be present from about 24 mM to about 36 mM, and more preferably from about 28 mM to about 33 mM. In one embodiment, the final concentration of sodium acetate in the final (combined) aqueous solution may be about or approximately 30 mM.

As noted above, additional buffering may be provided by bicarbonate ion. Bicarbonate may preferably be provided as the sodium salt, sodium bicarbonate $NaHCO_3$. Sodium bicarbonate may be present in the synthetic solution in an amount of between approximately 5 mM-40 mM, and more preferably between approximately 8 mM-25 mM. In one embodiment, the final concentration of bicarbonate in the final (combined) solution may be at least about 10 mM. In another embodiment, the concentration of bicarbonate may be about or approximately 20 mM.

Preferably, a buffer such as phosphate is also included in the storage solution described herein. In one embodiment, phosphate may be present from about 3 mM to about 11 mM, and more typically from about 6 mM to about 10 mM. Examples of sources of phosphate include (but are not limited to) sodium phosphate and/or potassium phosphate. In addition, the sodium phosphate and potassium phosphate used may include various forms of phosphate such as either or both monobasic and dibasic forms of phosphate. For example, a phosphate buffer having a phosphate concentration of 9.4 mM may contain approximately 7.2 mM (1.017 g/L) dibasic sodium phosphate anhydrous ($Na_2HPO_4$) and 2.2 (0.350 g/L) mM monobasic sodium phosphate dihydrate ($NaH_2PO_4.2H_2O$).

As noted above, the storage solution described herein may also include a selected concentration of magnesium ion. In one embodiment, magnesium ion may be present in the synthetic solution at concentrations close to plasma levels which will be about 3 mEq/L (1.5 mM). Magnesium ion at high cytosolic (intercellular) concentrations appears to play a role in resealing of the mitochondria [Petrollini V, Cola C, Bernardi P, Modulation of the mitochondria cyclosporin A-sensitive permeability transition pore, *J. Biol. Chem.* 1993; 268; 1011-6]. Consequently, magnesium ion in the medium should maintain the optimal intercellular magnesium levels in the white blood cells and may promote oxidative phosphorylation in the white blood cells and in so doing help maintain the pH of the medium. Preferably, magnesium ion may be added either as a chloride or a sulfate salt. In one embodiment magnesium ion may be present from about 0.05 mM to about 4 mM. More typically, magnesium ion may be present from about 0.1 mM to about 3.5 mM, or from about 0.5 mM to about 3.0 mM, or from about 1.0 mM to about 2.5 mM. In one particular embodiment, magnesium ion may be present from about 1.4 mM to about 2.2 mM. In one embodiment, the concentration of magnesium (chloride) in the final (combined) aqueous solution may be about 1.5 mM.

The storage solution described herein may also include a selected concentration of calcium ion. For example, calcium ion may be present in the aqueous solution. The presence of calcium ion in the medium may assist in maintaining intracellular magnesium ions. The synthetic storage media may initially contain about 0.5 mM to about 2.5 mM (1 to 5 mEq/) calcium ion. In one embodiment calcium ion may be present from about 0.05 mM to about 3 mM. More particularly, calcium ion may be present from about 0.4 mM to about 2.8 mM, or from about 0.6 mM to about 2.2 mM, or about 0.8 mM to about 1.2 mM.

The storage solution described herein may also include a selected concentration of potassium ion (from, for example, potassium chloride). The presence of potassium ion in the medium may assist in maintaining intracellular magnesium ion concentration. Potassium ion also appears to be involved in the transport of pyruvate across the mitochondria membrane for oxidative phosphorylation in the citric acid cycle (TCA cycle).

Preferably, potassium ion may be present from about 1 mM to about 10 mM. More preferably, potassium ion may be present from about 2 mM to about 9 mM, or from about 3 mM to about 8 mM, or from about 4 mM to about 7 mM, or from about 4.5 mM to about 6.5 mM. In one embodiment, the concentration of potassium (chloride) in the final (combined) aqueous solution may be about 5 mM.

The storage solution described herein may include a combination of magnesium ion, calcium ion, and potassium ion, or any other subcombinations of these three ions may be present in the storage solution. Where the storage solution is separated into two compartments of a container or container system, such as a neutral buffered physiological compartment and a carbohydrate compartment, one or more of the magnesium ion, calcium ion, and potassium ion may be contained in either or both compartments.

In the storage solution and storage media described herein, a carbohydrate is preferably included as a nutrient source of intermediate metabolites for production of energy. Glucose and other carbohydrates such as sucrose are nutrients for the white blood cells and can provide an important source of energy for white blood cells in storage by being the primary source of intermediate metabolites for the production of energy in the citric acid cycle. In one embodiment, the initial glucose concentration may be from about 0.5 mM to about 30 mM. More preferably, the initial glucose concentration may be from about 2 mM to about 22 mM. In some embodiments the initial glucose concentration may be from about 4 mM to about 20 mM. Preferably, the initial glucose concentration may be from about 6 mM to about 19 mM. In other embodiments the initial glucose concentration may be from about 10 mM to about 18 mM. In one embodiment, the concentration of glucose in the final (combined) aqueous solution may be about or approximately 16.8 mM. Carbohydrates such as sucrose can be used either in place of glucose or in combination with glucose as primary energy sources.

As noted above, the carbohydrate, for instance glucose, may be stored in a concentrated solution separately from the neutral buffered physiological salts. The concentrated carbohydrate solution may also contain other salts such as the calcium, magnesium, potassium, or sodium salts or any possible subcombination of these salts to raise the osmolarity of the concentrated carbohydrate compartment such that it is close to that of the buffered physiological compartment. To allow heat sterilization, such as autoclaving of the glucose solution, the glucose solution should be acidic for example with a pH between from about 4 to about 6.

As an example of a concentrated carbohydrate solution, 25 ml of the concentrated glucose solution may be combined with 275 ml of the buffered salt solution to produce 300 ml of aqueous solution. In this example, the concentrated glucose solution is 40 g/l glucose which results in a concentration of 3.3 g/L or 0.32 weight/weight glucose in the final white blood cell mixture.

Carbohydrate such as glucose, and more particularly D-glucose (dextrose) may be added to the platelet storage medium on the processing day (day 1) and/or later during storage, for instance on day 3 or 4 of storage. Addition of carbohydrate subsequent to the processing day may allow lower initial concentrations of carbohydrate to be used in the storage buffer, and as the carbohydrate is metabolized during storage, additional carbohydrate may be added. In this manner, lower concentrations of the carbohydrates are present in the storage medium during white blood cell storage, which as discussed herein, helps to suppress the production of lactic acid.

Thus, in one embodiment, the aqueous synthetic solution referred to herein as PAS-5, or PAS V, includes the following components in the following approximate concentrations (g/L):

TABLE 1

| Composition (g/L) | PAS-5 |
|---|---|
| Na$_3$Citrate•2H$_2$O | 2.94 |
| Na Acetate•3H$_2$O | 4.08 |
| NaH$_2$PO$_4$•2H$_2$O | 0.35 |
| NaH$_2$PO$_4$ | 1.02 |
| NaCl | 4.06 |
| KCl | 0.37 |
| MgCl$_2$ | 0.30 |
| Glucose | 3.33 |
| CaCl$_2$ | 0.15 |
| Na Bicarbonate | 0.75-1.70 |

In one embodiment, the white blood cell product may include approximately 0.1-500×10$^6$/ml white blood cells (depending, in part, on whether the white blood cells are being stored or cultured) and a storage medium including a synthetic storage solution where the storage solution includes approximately: 45-120 mM sodium chloride; 5-15 mM sodium citrate; 20-40 mM sodium acetate; 0.05-12 mM sodium phosphate; 0.05-3 mM magnesium ion; 0.05-10 mM potassium chloride; 5-40 mM sodium bicarbonate; and 0.5-30 mM glucose. The pH of the synthetic aqueous solution is approximately 7.0-8.0 and more typically, approximately 7.5. Some plasma may also be present in the storage medium and the white blood cell product, generally. Plasma may be present in less than 5% of the volume of the white blood cell product and, more preferably in less than 1% of such volume.

In a more particular embodiment, the white blood cell product may include approximately 0.1-500×10$^6$/ml white blood cells and a storage medium including a synthetic storage solution wherein the synthetic storage solution includes approximately: 69 mM sodium chloride; approximately 10 mM sodium citrate; approximately 30 mM sodium acetate; approximately 9.3 mM sodium monobasic phosphate dihydrate and diabasic sodium phosphate anhydrous; approximately 1.5 mM magnesium chloride, approximately 5 mM potassium chloride, approximately 16.8 mM glucose (dextrose) and at least approximately 10 mM sodium bicarbonate. The pH of the solution is approximately 7.0-8.0 and more typically, approximately 7.5. Some plasma, in the amounts set forth above, may also be present.

The storage media allows the stored white blood cells to preserve functionality and viability over 24 hours and up to at least 72 hours. The storage solution described above may also be used in the culturing of white blood cells. Thus, the solution(s) described above, when used for culturing, may be supplemented with approximately 10-50% human serum.

When the synthetic aqueous solutions disclosed herein are used as storage solutions (without supplementation with certain culturing additives such as human serum) the white blood cell products maintain viability and have acceptable levels of apoptotic cells for up to at least about 72 hours when measured by the viability assays using Annexin and 7-AAD. For example, white blood cells (approximately 12×10$^6$/ml at Day 0) washed with and/or stored in the solutions described above display less than 30% apoptosis as measured by the viability assays using Annexin V+ after 72 hours, and the percentage of viable white blood cells was above 90% after 72 hours as measured by the 7-AAD viability assay.

By way of example, but not limitation, methods of collecting, washing and storing white blood cells using the storage solutions and media are briefly described below.

Figure 2:
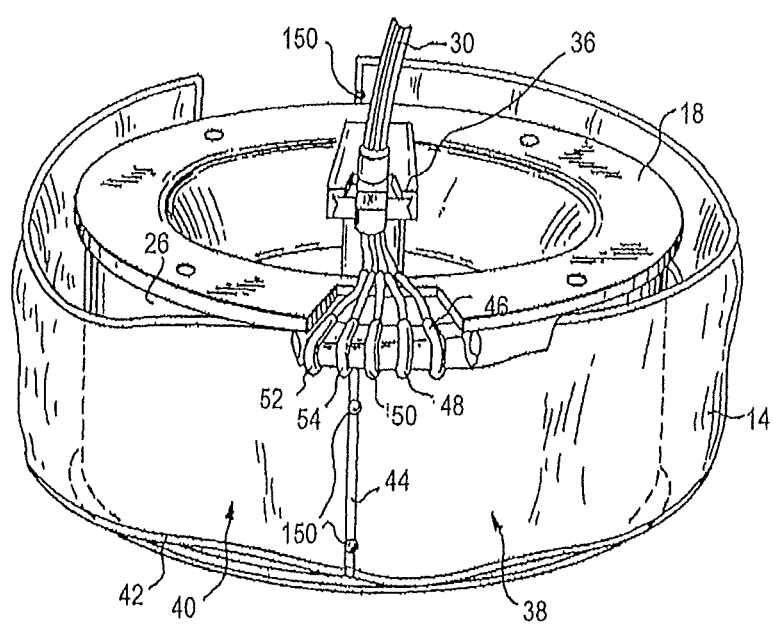
FIG. 2 is a perspective view of a blood collection chamber for use with a rotor of the apheresis device of FIG. 1.
Figure 3:
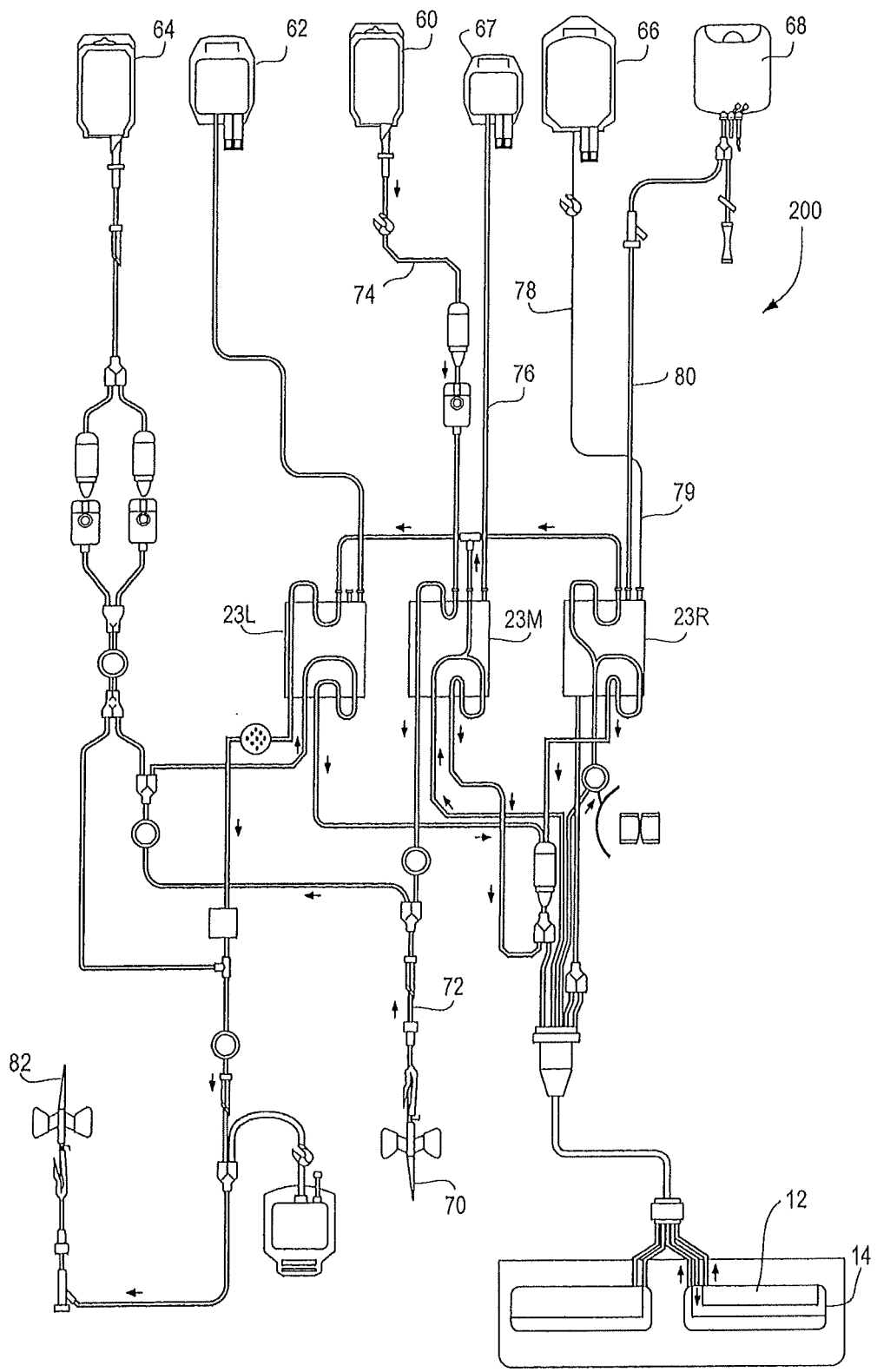
FIG. 3 is a schematic diagram of a fluid processing set for use with the apheresis device of FIG. 1 for the collection of white blood cells, such as mononuclear cells.

FIGS. 1-3 show a representative blood centrifuge 10 with fluid circuit 200 mounted thereon (FIG. 1), the fluid circuit (FIG. 3) having a blood processing container 14 (see FIG. 2) defining a separation chamber suitable for harvesting white blood cells from whole blood. As shown in FIG. 1, a disposable processing set or fluid circuit 200 (which includes container 14) is mounted on the front panel of centrifuge 10. The processing set (fluid circuit 200) includes a plurality of processing cassettes 23L, 23M and 23R with tubing loops for association with peristaltic pumps on device 10. Fluid circuit 200 also includes a network of tubing and pre-connected containers for establishing flow communication with the patient and for processing and collecting fluids and blood and blood components, as shown in greater detail in FIG. 3. As seen in FIGS. 1 and 3, disposable processing set 200 may include a container 60 for supplying anticoagulant, a waste container 62 for collecting waste from one or more steps in the process for treating and washing mononuclear cells, a container 64 for holding the storage solution described herein, a container 66 for collecting plasma and a container 68 for collecting the white blood cells.

With reference to FIG. 3, fluid circuit includes inlet line 72, an anticoagulant (AC) line 74 for delivering AC from container 60, an RBC line 76 for conveying red blood cells from chamber 12 of container 14 to container 67, a platelet-poor plasma (PPP) line 78 for conveying PPP to container 66 and line 80 for conveying white blood cells to and from separation chamber 14 and collection container 68. As will be known to those of skill in the art, the blood processing set includes one or more venipuncture needle(s) for accessing the circulatory system of the patient. As shown in FIG. 3, fluid circuit 200 includes inlet needle 70 and return needle 82. In an alternative embodiment, a single needle can serve as both the inlet and outlet needle.

Fluid flow through fluid circuit 200 is preferably driven, controlled and adjusted by a microprocessor-based controller in cooperation with the valves, pumps, weight scales and sensors of device 10 and fluid circuit 200, the details of which are described in U.S. Pat. No. 6,027,657, the contents of which are incorporated herein by reference.

Separation chamber 12 is defined by the walls of a flexible processing container 14 carried within an annular gap defined by a rotating spool element 18 (FIG. 2) and an outer bowl element (not shown). The processing container 14 takes the form of an elongated tube which is wrapped about the spool element 18 before use. The bowl and spool element 18 are pivoted on a yoke between an upright position and a suspended position, also not shown.

When upright, the bowl and spool element 18 are presented for access by the user. A mechanism permits the spool 18 and bowl elements to be opened so that the operator can wrap the container 14 about the spool element 18, as shown in FIG. 2. Pins 150 on the spool element 18 engage cutouts on the container 14 to secure the container 14 on the spool element 18. In operation, the centrifuge 10 rotates the suspended bowl and spool element 18 about an axis, creating a centrifugal field within the processing chamber of container 14.

The radial boundaries of the centrifugal field are formed by the interior wall of the bowl element and the exterior wall 26 of the spool element 18 shown in FIG. 2. The interior bowl wall defines the high-G wall. The exterior spool wall 26 defines the low-G wall. Further details of the mechanism for causing relative movement of the spool 18 and bowl elements as just described are disclosed in U.S. Pat. No. 5,360,542 entitled "Centrifuge With Separable Bowl and Spool Elements Providing Access to the Separation Chamber," which is also incorporated herein by reference.

Turning now to the method of collecting white blood cells, with reference to FIG. 3, whole blood is withdrawn from a patient through inlet needle 70 and introduced into the separation chamber 12 of container 14 of processing set 200, where the whole blood is subjected to a centrifugal field. The centrifugal field will separate the target cell population, i.e., white blood cells, from red blood cells, platelets and plasma. As discussed above, the components such as red blood cells and platelets may be returned to the patient or may be diverted to a container (e.g., container 67) for further processing.

Collection of the white blood cells may proceed in one or more cycles. The number of processing cycles conducted in a given therapeutic procedure will depend upon the total volume of white blood cells to be collected. For example, in a representative procedure, five collection cycles may be performed sequentially. During each cycle about 1500-3000 ml of whole blood can be processed to obtain a white blood cell volume of about 3 ml per cycle and a total volume of 15 ml of white blood cells. Further details of one example of white blood cell collection are described in U.S. Pat. No. 6,027,657, the contents of which are incorporated herein by reference. Of course, the collection of white blood cells is not limited to the method or the apparatus described above. White blood cells may be collected in any manner known to those of skill in the art, including centrifugal separation devices other than the one depicted herein and described above and other leukocyte collection devices.

White blood cells may be returned to separator 10 (and more specifically, the separation chamber 12 of container 14) for further processing such as washing. For example, one of the pumps associated with cassette 23R may be actuated (automatically by the controller or under the manual control of the operator) to withdraw the treated white blood cells from container 68 and introduce the white blood cells into chamber 12 of container 14. Once inside chamber 14, the white blood cells may be concentrated to effectively "wash" the white blood cells. More specifically, supernatant is separated from the concentrated and treated cells and diverted to a waste container. The concentrated cells may be resuspended or reconstituted in the synthetic solution described herein or other suitable resuspension media (e.g., plasma, saline).

Where the concentrated cells are combined with wash solution, the white blood cells with wash solution within the chamber 12 (of container 14 of the disposable processing set 200) are separated from remaining supernatant under the field of centrifugal force. It will be appreciated that the step of washing the white blood cells may be repeated, as necessary. The synthetic solutions described herein may be suitable for washing and storing white blood cells.

Figure 4:
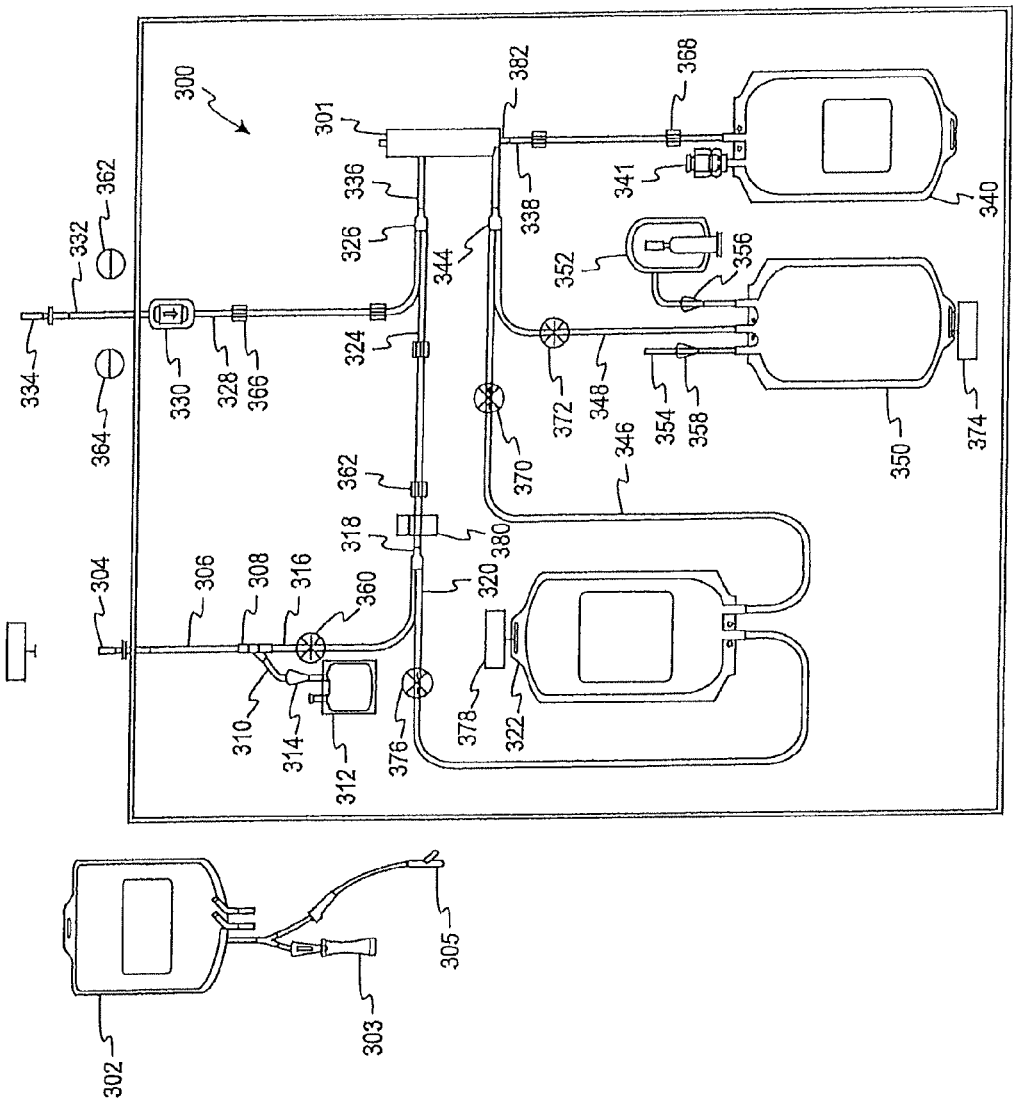
FIG. 4 is a schematic diagram of a disposable processing set mountable on the panel of the device of FIG. 5, useful in the washing of white blood cells.
Figure 5:
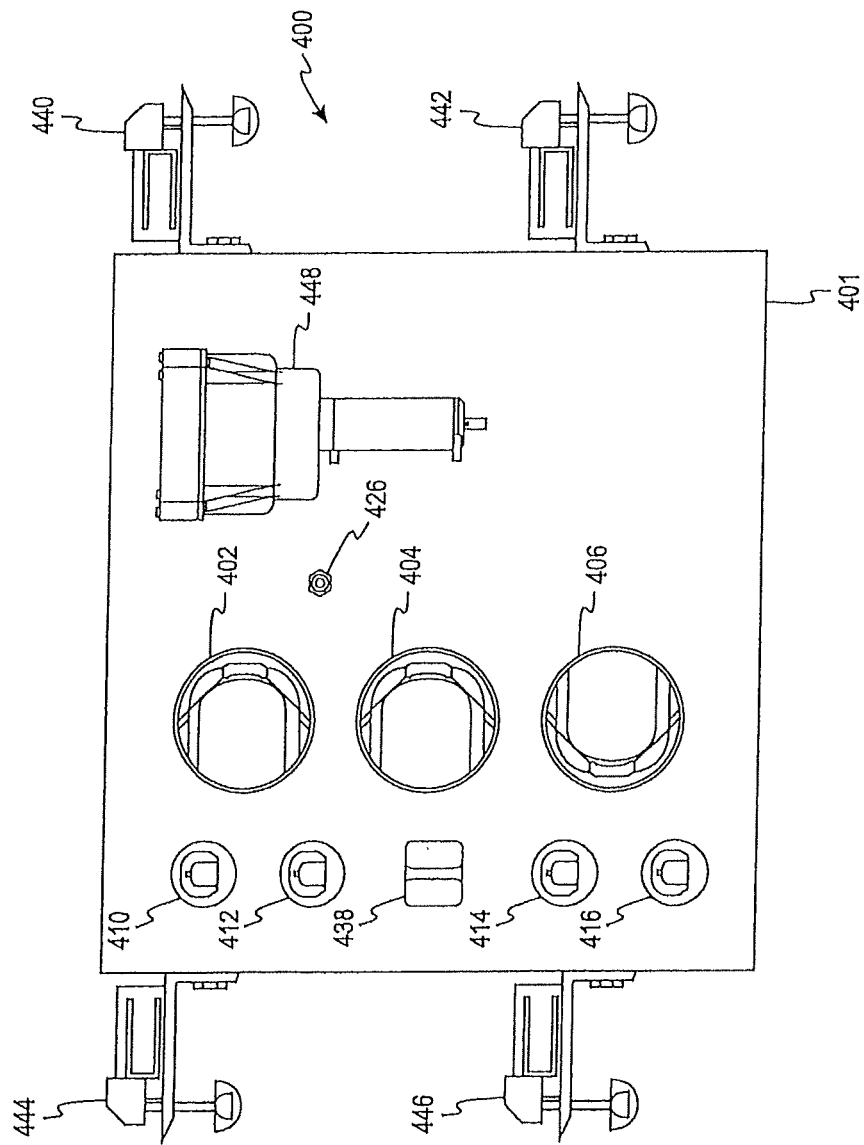
FIG. 5 is a plan view of the front panel of a separation device useful in the washing of white blood cells onto which the processing set of FIG. 4 is mounted.

In another embodiment, the collected white blood cells may be washed using a different device such as a device that utilizes a spinning membrane. In accordance with the present disclosure, FIGS. 4-5 show a disposable processing set and hardware components of an exemplary spinning membrane system useful in the washing of biological cells, such as, but not limited to white blood cells. Spinning membrane separators and methods and systems for washing cells, such as white blood cells, are described in International Patent Application Serial No. PCT/US2012/028522, filed Mar. 9, 2012, the contents of which are incorporated herein by reference. Thus, it will be appreciated that the details of the methods and systems useful in the washing of white blood cells with the synthetic solution described herein as the wash solution may be found in International Patent Application Serial No. PCT/US2012/028522, filed Mar. 9, 2012 and will not be repeated here.

Briefly, however, as shown in FIG. 4, separator 301 is integrated into the exemplary disposable processing set 300. The white blood cells to be washed are typically provided in a source container 302 (shown in FIG. 4, as disconnected from the disposable set). In one embodiment, source container 302 may be collection container 68 that includes white blood cells collected using the system of FIGS. 1-3. As noted above, source container 302 may be attached (in sterile fashion) at the time of use. Source container 302 has one or more receiving ports 303, 305, one of which may be adapted to receive spike connector 304 of disposable set 300. More particularly, source container 302 is connected to the disposable set 300 via the spike connector 304, which is connectable to access port 303. More preferably, however, source containers (and the fluid therein) may be free of a spike connector and accessed in a sterile manner by employing sterile docking devices, such as the BioWelder, available from Sartorius AG, or the SCD IIB Tubing Welder, available from Terumo Medical Corporation. A second access port 305 may also be provided for extracting fluid from the source bag 302.

In accordance with the system disclosed herein, a wash solution may be attached (or pre-attached) to set 300. As shown in FIG. 4, tubing 332 (defining a flow path) preferably includes spike connector 334 at its end. Spike connector 334 is provided to establish flow communication with a container of a wash fluid, such as the synthetic solution disclosed herein. The wash solution flows from the wash fluid source, through the second spike connector 334, through tubing segment 332, where it may be filtered by the sterile barrier filter 330 described above, and then passes through tubing 128 to the input of the branched-connector 326 described above.

Tubing segment 336 defines a flow path connected at one end to a port of branched-connector 326 and to an inlet port of the separator 301. Preferably, in accordance with this embodiment, separator 301 is a spinning membrane separator. The spinning action of the device causes cells to separate from the remainder of the fluid in which it was suspended and/or from the wash solution. Preferably, the supernatant and the wash solution pass through the membrane while the desired cells are concentrated within the chamber of the separator. The waste resulting from the separation, which includes wash medium and supernatant medium, exits port 382 and flows through tubing 338 to waste product container 340. The washed white blood cells are collected in container 350.

FIG. 5 shows the front panel 401 of separation device 400; i.e., the hardware, which receives the processing set described above. Device 401 includes peristaltic pumps 402, 404 and 406. Pump segments 362, 366 and 368 from the above-described processing set are selectively associated with peristaltic pumps 402, 404, and 406. The peristaltic pumps articulate with the fluid set of FIG. 23 at the pump segments 362, 366 and 368 and advance the cell suspension within the disposable set, as will be understood by those of skill in the art.

White blood cell products that may be washed with the synthetic solutions of the present disclosure (e.g., PAS 5) and/or in accordance with the methods described above (by centrifugal separator, spinning membrane separator or other device) may include freshly collected, but not previously stored, white blood cells. In addition, the white blood cell products that may be washed with the aqueous synthetic solutions of the present disclosure (e.g., PAS 5) and/or in accordance with the methods described above may include white blood cells that have been stored or cultured in either plasma, saline, Ringers solution, Plasmalyte, the storage medium that includes the aqueous storage solution disclosed herein (and other supplements), a culture media or a media that includes other agents used in the processing of white blood cells, or any other medium suitable for the storage or culturing of white blood cells such as mononuclear cells. Thus, the source of the white blood cell product (e.g., in container 68 of FIGS. 1 and 3, or container 302 in FIG. 4) may be white blood cells stored in plasma, white blood cells stored in RPMI 1640 (with human serum), white blood cells stored in PAS 5 or other comparable additive solution supplemented with human serum, white blood cells with cryopreservative as disclosed in U.S. Provisional Patent Application Ser. No. 61/613,239, filed Mar. 20, 2012, the contents of which are incorporated herein by reference, white blood cells with residual photopheresis agent such as 8-methoxypsoralen, as disclosed in U.S. Provisional Patent Application Ser. No. 61/591,596, filed Jan. 27, 2012, the contents of which are incorporated herein by reference. U.S. Pat. application Publication Nos. US2013/0197419, filed Jan. 3, 2013, and US2013/0252227, filed Feb. 6, 2013, respectively, are the published non-provisiona; applications which claim the benefit of the above-referenced provisional applications.

EXAMPLE 1

Preparation of Synthetic Storage Solution

In one embodiment, the partitioning of the ingredients of the synthetic storage solution may consist of 2 parts—part 1, a neutral buffered physiological compartment containing one set of components such as the citrate, acetate, phosphate, sodium ion and optionally magnesium ion, calcium ion, potassium ion, bicarbonate ion, and part 2, an acidic carbohydrate compartment containing the dextrose, and optionally calcium ion, magnesium ion and potassium ion with both compartments having similar osmolarity. In Table 2 an example of a synthetic media with two compartments is presented. The concentrations and/or amounts of the components are as previously described.

TABLE 2

Composition of white blood cell storage solution in a three bag assembly (in g/Liter)

| Buffered Physiological Compartment | |
|---|---|
| Bag 1 containing (in g/L) | 275 ml |
| $Na_3$ Citrate•$2H_2O$ | |
| Na Acetate $3H_2O$ | |
| $NaH_2PO_4$•$2H_2O$ | |
| $Na_2HPO_4$ | |
| KCl | |
| NaCl | |
| $NaHCO_3$ | |
| pH | 7.0-7.4 |
| Osmolarity | 300 mOsm/L |
| Bag 2 containing (in g/L) | 25 ml |
| Carbohydrate Compartment | |
| Dextrose Monohydrate | |
| $CaCl_2$•$2H_2O$ | |
| $MgCl_2$•$6H_2O$ | |
| pH | 4-6 |
| Osmolarity | 292 or 328 mOsm/L |
| Bag 3: | final storage container (PL146) |

Bicarbonate, such as sodium bicarbonate may be added directly to Bag 3 or be included in Bag 1 as shown.

Once combined, the storage solution described herein (in 300 mL volume) may contain, for example, approximately 16.8 mM dextrose monohydrate (D-glucose), 0 or 1.0 mM calcium chloride, approximately 1.5 mM magnesium chloride, approximately 10 mM sodium citrate, approximately 30 mM sodium acetate, approximately 9.4 mM sodium phosphate (7.2 mM dibasic sodium phosphate anhydrous and 2.2 mM monobasic sodium phosphate dihydrate), approximately 5 mM potassium chloride, approximately 69.55 mM sodium chloride, and approximately 8-25 mM of sodium bicarbonate and more preferably approximately 10-20 mM. This aqueous storage solution may then be combined with the white blood cell product containing residual plasma to yield a white blood cell product or suspension for storage with a desired plasma ratio for instance between about 1% and 10%, such as about 5% and even more preferably less than 1%. Some methods of preparing white blood cells such as apheresis type collection or methods that involve washing steps may result in high concentrations of white blood cells with relatively small volumes of plasma.

EXAMPLE 2

White blood cells were collected from healthy male donors using the AMICUS® Separator followed by purification using a ficoll gradient. Cells were resuspended at $1-2\times10^6$/ml in either RPMI1640 medium supplemented with 2 mM glutamine and 10% human serum (HS) (control) or PAS 5 (as set forth in Table 1) supplemented with 10-30% human serum. Cells were cultured in 25 ml flasks at 37° C. in a humidified chamber with 5% $CO_2$ for up to 72 hours. After 24, 48 and 72 hours in culture, samples were assayed for lymphocyte apoptosis. Apoptosis was measured as the % of CD45+/Annexin V positive cells in the lymphocyte/side scatter gate.

A total of 10 white blood cell products were tested. The results are shown in Table 3 below.

TABLE 3

| % Apoptotic Lymphocytes (Mean ± SD) | n | 24 Hours | 48 Hours | 72 Hours |
|---|---|---|---|---|
| RPMI + Glu, 10% HS (control) | 10 | 8 ± 2 | 13 ± 2 | 15 ± 2 |
| PAS-5 + 10% HS | 7 | 11 ± 3 | 23 ± 3 | 32 ± 4 |
| PAS-5 + 20% HS | 6 | 8 ± 2 | 18 ± 3 | 30 ± 6 |
| PAS-5 + 30% HS | 4 | 8 ± 2 | 18 ± 1 | 25 ± 2 |

EXAMPLE 3

Figure 6:
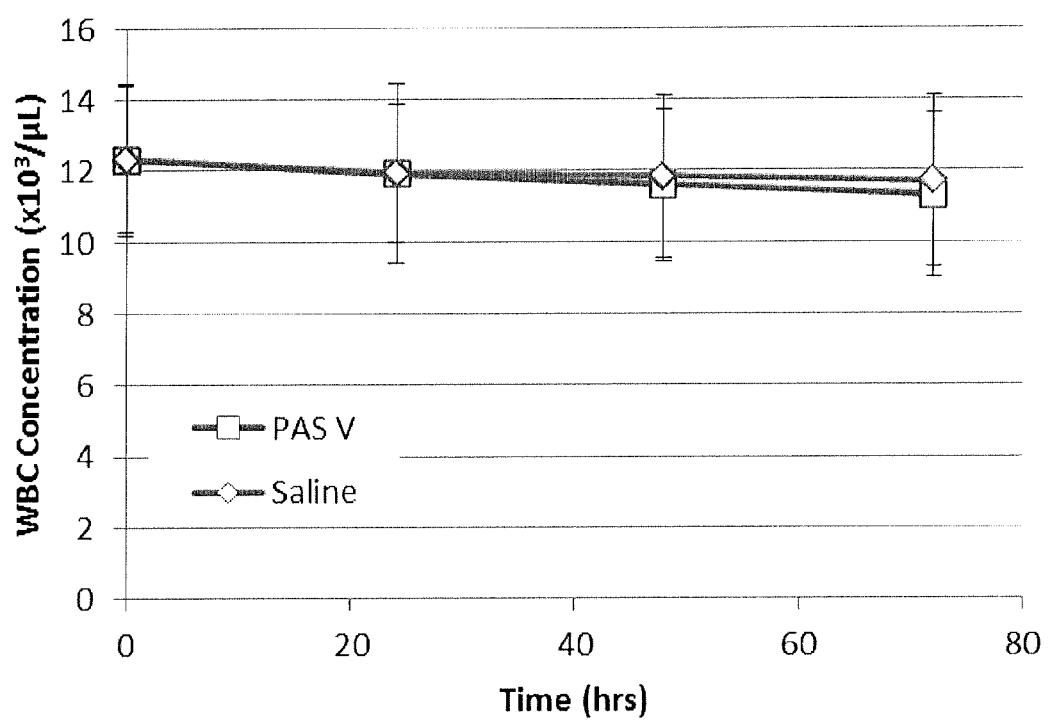
FIG. 6 is a graph showing the concentration of white blood cells washed with and stored in (a) saline and (b) the synthetic aqueous solution disclosed herein over a 72 hour storage period.
Figure 7:
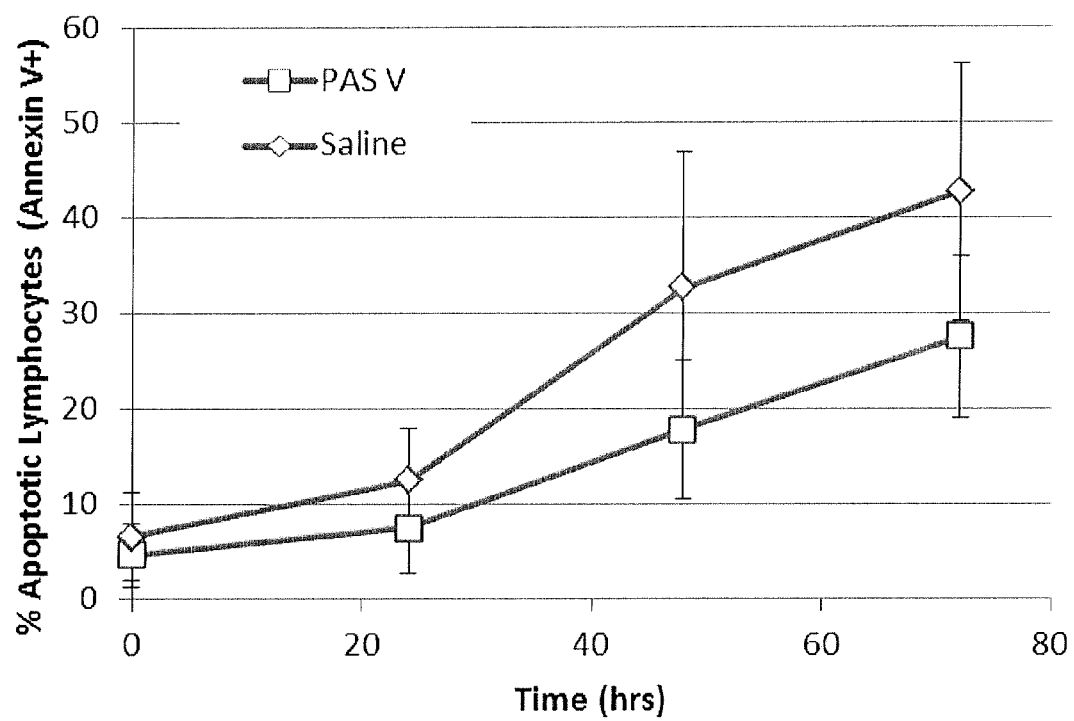
FIG. 7 is a graph showing the percentage of apoptotic lymphocytes in lymphocytes washed with and stored in (a) saline and (b) the synthetic aqueous solution disclosed herein over a 72 hour storage period.
Figure 8:
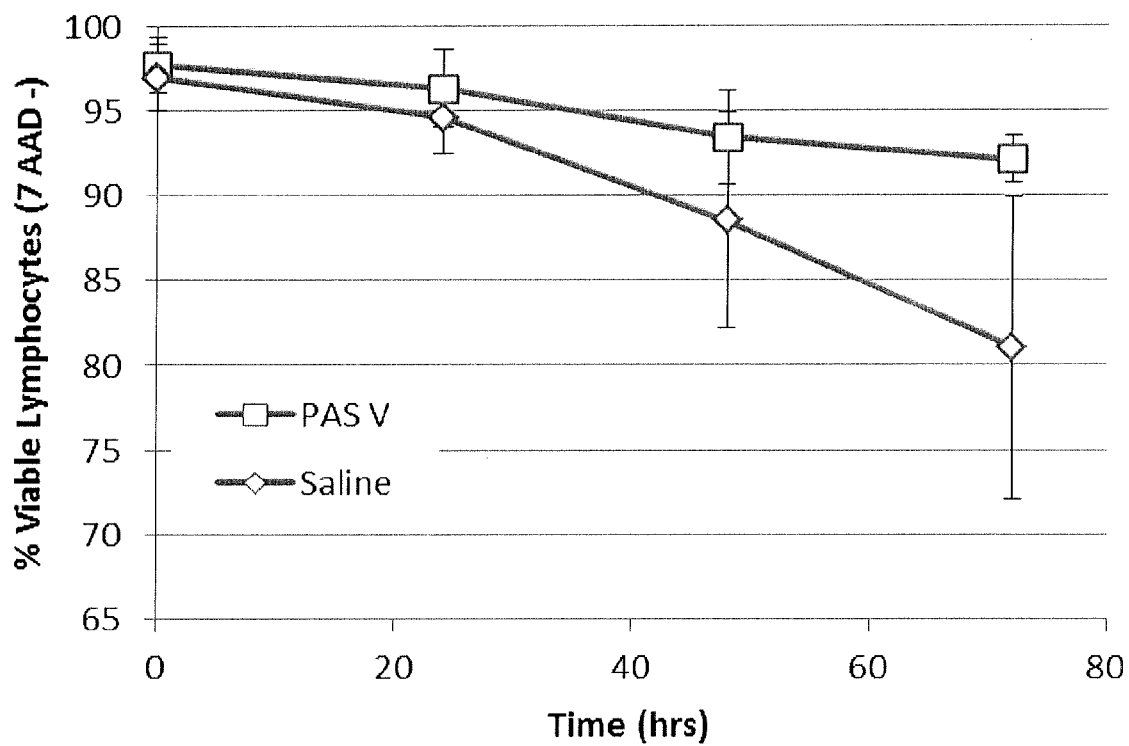
FIG. 8 is a graph showing the percentage of viable lymphocytes (as measured by the 7-AAD assay) in lymphocytes washed with and stored in (a) saline and (b) the synthetic aqueous solution disclosed herein over a 72 hour storage period.

White blood cells were obtained from the AMICUS® Separator with the following settings: 1,500 ml/cycle, 2 cycles, WBC/RBC offset of 1.5/6.0, storage fluid volume equal 400 ml. The white blood cell product was split into two equivalent 200 ml volumes and one unit was washed with saline and the other unit with PAS 5 (as generally described in Table 1 above), both washing processes utilizing a spinning membrane separation (N=5 pairs) of the type described above. The membrane used was a 4.0 µM polycarbonate membrane. Each of the white blood cell products was introduced into a spinning membrane separator where the white blood cells were separated from the supernatant. A 10:1 concentration of the cell supernatant (i.e., 1 log reduction in supernatant) was achieved. The concentrated cells were then diluted back to the original white blood cell product volume (e.g., 200 ml) with either saline or the synthetic aqueous solution (PAS 5) disclosed herein. The diluted white blood cell products were then reintroduced into the spinning membrane separator where the white blood cell product was again concentrated, yielding a final and total 99% reduction in the supernatant. Additional saline and PAS 5, respectively, was added to the concentrated white blood cells to arrive at a final storage volume of 200 ml. The washed white blood cells were stored undisturbed in 1 L PL2410 containers at 4° C. up to 72 hours. At T=0 (immediately following washing), 24, 48 and 72 hours, cell samples were removed from each white blood cell product for apoptosis/viability assay and cell count. Lymphocyte apoptosis and viability were measured as the % of CD45 positive cells in the lymphocyte/side scatter gate that stained positive for Annexin V or 7-AAD, respectively. The results of this study are set forth in FIGS. 6-8.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

We claim:

1. A method of processing white blood cells, said method comprising:
   a) introducing white blood cells from a source of white blood cells into a separation chamber of a separation device, said source comprising white blood cells that have been previously and substantially separated from platelets and red blood cells;
   b) separating said white blood cells from supernatant to obtain a concentrate of white blood cells;
   c) combining said white blood cell concentrate with a storage media including a solution comprising:
      approximately 45-120 mM sodium chloride;
      approximately 5-15 mM sodium citrate;
      approximately 20-40 mM sodium acetate; approximately 0.05-12 mM of sodium phosphate;
      approximately 0.05-3 mM magnesium ion;
      approximately 0.05-10 mM potassium chloride;
      approximately 5-40 mM sodium bicarbonate; and
      approximately 0.5-30 mM glucose.

2. The method of claim 1 further comprising adding a wash solution to said white blood cells prior to said combining, said wash solution comprising:
   approximately 45-120 mM sodium chloride;
   approximately 5-15 mM sodium citrate;
   approximately 20-40 mM sodium acetate;
   approximately 0.05-3 mM magnesium ion;
   approximately 0.05-10 mM potassium chloride;
   approximately 5-40 mM sodium bicarbonate;
   approximately 0.5-30 mM glucose;
   and concentrating said white blood cells by removing supernatant.

3. The method of claim 2 comprising introducing said wash solution into said separation device.

4. The method of claim 1 further comprising storing said white blood cells in said solution for up to at least 72 hours.

5. The method of claim 4 comprising storing said white blood cells at a temperature of about 46° C.

6. The method of claim 4 wherein the number of viable white blood cells after approximately 72 hours of storage is greater than 90%, as measured by 7-AAD assay.

7. The method of claim 4 wherein the level of apoptosis of said white blood cells after approximately 72 hours of storage is approximately 30%, as measured by the Annexin V assay.

8. The method of claim 1 wherein said source of white blood cells comprises a white blood cell product further comprising a culture medium.

9. The method of claim 1 wherein said white blood cells are present in a concentration of approximately $5-50 \times 10^6$ per ml.

10. The method of claim 1 wherein said white blood cells are present in a concentration of approximately $0.1-500 \times 10^6$/ml.

11. The method of claim 10 wherein said white blood cells are present in a concentration of approximately $1-2 \times 10^6$/ml.

12. The method of claim 10 wherein said white blood cells are present in a concentration of approximately $10-500 \times 10^6$/ml.

* * * * *